(12) United States Patent
Mehrotra et al.

(10) Patent No.: US 11,850,029 B2
(45) Date of Patent: Dec. 26, 2023

(54) TONOMETRY BASED BLOOD PRESSURE MEASUREMENTS USING A TWO-DIMENSIONAL FORCE SENSOR ARRAY

(71) Applicant: Northwestern University, Evanston, IL (US)

(72) Inventors: Sanjay Mehrotra, Winnetka, IL (US); Ilya Mikhelson, Wilmette, IL (US); Alan Varteres Sahakian, Northbrook, IL (US)

(73) Assignee: Northwestern University, Evanston, IL (US)

( * ) Notice: Subject to any disclaimer, the term of this patent is extended or adjusted under 35 U.S.C. 154(b) by 102 days.

(21) Appl. No.: 17/385,216

(22) Filed: Jul. 26, 2021

(65) Prior Publication Data

US 2022/0039676 A1 Feb. 10, 2022

Related U.S. Application Data

(62) Division of application No. 15/627,911, filed on Jun. 20, 2017, now Pat. No. 11,109,768.

(60) Provisional application No. 62/375,524, filed on Aug. 16, 2016, provisional application No. 62/355,017, filed on Jun. 27, 2016.

(51) Int. Cl.
*A61B 5/021* (2006.01)
*A61B 5/00* (2006.01)
*A61B 5/02* (2006.01)

(52) U.S. Cl.
CPC ........ *A61B 5/02108* (2013.01); *A61B 5/6824* (2013.01); *A61B 5/02* (2013.01); *A61B 2562/0247* (2013.01)

(58) Field of Classification Search
CPC ..... A61B 5/02108; A61B 5/6824; A61B 5/02; A61B 2562/0247
USPC ....................................................... 600/301
See application file for complete search history.

(56) References Cited

U.S. PATENT DOCUMENTS

| | | | |
|---|---|---|---|
| 6,662,032 B1 * | 12/2003 | Gavish | A61B 5/4884 600/323 |
| 2008/0001735 A1 * | 1/2008 | Tran | G16H 50/20 340/539.22 |
| 2011/0004110 A1 * | 1/2011 | Shusterman | G16H 50/20 600/509 |

* cited by examiner

*Primary Examiner* — Aaron F Roane
(74) *Attorney, Agent, or Firm* — Bell & Manning, LLC (57) ABSTRACT

Representative methods, apparatus and systems are disclosed for blood pressure and other vital sign monitoring using arterial applanation tonometry, including ambulatory blood pressure and other vital sign monitoring. A representative system comprises a wearable apparatus. The various embodiments measure blood pressure and other vital sign monitoring using a plurality of pressure sensors of a pressure sensor array, with one or more of the pressure sensors 140 applanating an artery, such as a radial artery. In a first embodiment, a pressure sensor signal is utilized which has the highest cross-coherence with the signals of its nearest pressure sensor neighbors of the pressure sensor array. In a second embodiment, Kalman filtering is utilized for the pressure sensor signals from the pressure sensor array.

6 Claims, 9 Drawing Sheets

FIG. 6C

TONOMETRY BASED BLOOD PRESSURE MEASUREMENTS USING A TWO-DIMENSIONAL FORCE SENSOR ARRAY

CROSS-REFERENCE TO RELATED APPLICATIONS

This application is a Divisional Patent Application that claims priority to U.S. patent application Ser. No. 15/627,911 filed on Jun. 20, 2017, which claims the benefit of and priority to U.S. Provisional Patent Application No. 62/355,017, filed Jun. 27, 2016, inventors Sanjay Mehrotra et al., titled "Tonometry Based Blood Pressure Measurements Using a Two-Dimensional Force Sensor Array", and further claims the benefit of and priority to U.S. Provisional Patent Application No. 62/375,524, filed Aug. 16, 2016, inventors Sanjay Mehrotra et al., titled "Tonometry Based Blood Pressure Measurements Using a Two-Dimensional Force Sensor Array", which are commonly assigned herewith, and all of which are hereby incorporated herein by reference in their entireties with the same full force and effect as if set forth in their entireties herein.

STATEMENT REGARDING FEDERALLY SPONSORED RESEARCH OR DEVELOPMENT

This invention was made with government support under U01 EB020589 awarded by the National Institutes of Health. The government has certain rights in the invention.

FIELD OF THE INVENTION

The present invention, in general, relates to blood pressure and other vital sign monitoring, and more particularly, relates to an apparatus, system and method for noninvasive, ambulatory blood pressure and vital sign monitoring.

BACKGROUND OF THE INVENTION

High blood pressure ("BP"), also referred to as hypertension, is a major cardiovascular risk factor contributing to various medical conditions, diseases, and events such as heart attacks, heart failure, aneurisms, strokes, and kidney disease, for example. While hypertension generally is medically treatable, the rates for detection and control of high BP remain low, especially because high BP may not cause any other symptoms which would be noticeable to an individual. As a result, there is a well-established need for blood pressure and other vital sign monitoring, whether such monitoring occurs in a hospital setting, a physician's office, a patient's home or office, and whether such monitoring occurs while the individual is at rest or engaged in an activity, such as sitting, walking, exercising, or sleeping, also for example.

Hypertension is estimated to cause 7.5 million yearly deaths, about 12.8% of all deaths [1] worldwide. In today's clinical practice, blood pressure (BP) is typically measured in an office setting using cuff-based devices. Despite training, such devices can be cumbersome and difficult to use. Office-based blood pressure has limited sensitivity (75%) and specificity (75%) as a sole test for diagnosing hypertension, and studies have shown that ambulatory blood pressure predicts mortality significantly better than clinical blood pressure [3]. Clinical practice guidelines and professional organizations increasingly emphasize 24-hour ambulatory blood pressure monitoring and home-based self-monitoring of blood pressure to aid in the diagnosis and management of hypertension [3, 4]. Cuff-based BP measurement systems are cumbersome for ambulatory and everyday use. The force-pressure measurement principles of applanation tonometry are well established (see, e.g. [4]) and date back to the 1960s with the creation of a simple, single transducer [5].

CITED REFERENCES

[1] Raised Blood Pressure. [cited 2013 September]; Available from: http://www.who.int/gho/ncd/risk_factors/blood_pressure_prevalence_text/en/.
[2] NICE, UK National Institute for Health and Care Excellence. NICE clinical guideline 127. Hypertension: clinical management of primary hypertension in adults . . . 2011.
[3] Drzewiecki, G. M., J. Melbin, and A. Noordergraaf, Arterial tonometry: review and analysis. Journal of biomechanics, 1983. 16(2): p. 141-152.
[4] Pressman, G. L. and P. M. Newgard, A Transducer for the Continuous External Measurement of Arterial Blood Pressure. IEEE Trans Biomed Eng, 1963. 10: p. 73-81.
[5] Joseph S Eckerle, Tonometry, arterial, in Encyclopedia of medical devices and instrumentation. 2006.

BRIEF SUMMARY OF THE INVENTION

The representative embodiments of the present invention provide numerous advantages. The disclosed invention uses a signal and data processing approach that can be used for ambulatory blood pressure measurement. The signal and data processing approach uses a two-dimensional array of pressure sensors for applanating an artery and combines the information generated from these pressure sensors to estimate an individual's ambulatory blood pressure. The two-dimensional array of pressure sensors increases the likelihood of obtaining accurate pressure sensor data from an applanated artery. The approach is particularly advantageous in an ambulatory setting, where it may be difficult to locate an individual's artery, and the signals generated may be noisy.

A representative method embodiment for determining a blood pressure of a subject human being for ambulatory monitoring is disclosed, with the representative method comprising: using a pressure sensor array having a plurality of pressure sensors spaced-apart in at least two dimensions, applanating an artery; receiving a plurality of pressure sensor signals, one or more of the pressure sensor signals having data representing amplitudes of one or more arterial pressure waves; determining a frequency content of each of the one or more of the pressure sensor signals having data; selecting one or more periodic pressure sensor signals to form a first plurality of selected pressure sensor signals; selecting one or more periodic pressure sensor signals within a selected or predetermined deviation, such as a standard deviation, of a mean of the first plurality of selected pressure sensor signals to form a second plurality of selected pressure sensor signals; using one or more periodic pressure sensor signals from the second plurality of selected pressure sensor signals, determining a systolic blood pressure value and a diastolic blood pressure value.

A representative method may further comprise: for each periodic pressure sensor signal of the second plurality of selected pressure sensor signals, determining a cross-coherence with each nearest neighbor pressure sensor signal; and selecting a periodic pressure sensor signal having a highest mean cross-coherence. For such a representative embodiment, the step of determining the systolic blood pressure value and the diastolic blood pressure value may further comprise: determining the systolic blood pressure value as a maximum of the periodic pressure sensor signal having a highest mean cross-coherence; and determining the diastolic blood pressure value as a minimum of the periodic pressure sensor signal having a highest mean cross-coherence.

A representative method may further comprise: determining the mean and standard deviation of the first plurality of selected pressure sensor signals.

A representative method also may further comprise: performing a first filtering of the plurality of pressure sensor signals to eliminate one or more pressure sensor signals below a selected or predetermined threshold, such as those which do not have relevant pressure data.

A representative method may further comprise: sampling and converting the plurality of pressure sensor signals into a corresponding plurality of digital amplitude values.

A representative method may further comprise: using one or more periodic pressure sensor signals from the second plurality of selected pressure sensor signals, determining a heart rate.

A representative method may further comprise: performing a Kalman filtering of the second plurality of selected pressure sensor signals; determining the systolic blood pressure value as a maximum of the Kalman filter data; and determining the diastolic blood pressure value as a minimum of the Kalman filter data.

A representative method may further comprise one or more of the following: displaying the determined blood pressure value and other vital sign information to the user; transmitting the determined blood pressure value and other vital sign information to a central location; and/or storing the determined blood pressure value and other vital sign information in a memory circuit.

A representative apparatus embodiment is disclosed for determining a blood pressure of a subject human being for ambulatory monitoring, the representative apparatus embodiment comprising: a pressure sensor array having a plurality of pressure sensors spaced-apart in at least two dimensions; and a processor coupled to the pressure sensor array, the processor adapted to receive a plurality of pressure sensor signals, one or more of the pressure sensor signals having data representing amplitudes of one or more arterial pressure waves; determine a frequency content of each of the one or more of the pressure sensor signals having data; select one or more periodic pressure sensor signals to form a first plurality of selected pressure sensor signals; select one or more periodic pressure sensor signals within a selected or predetermined deviation, such as a standard deviation, of a mean of the first plurality of selected pressure sensor signals to form a second plurality of selected pressure sensor signals; and using one or more periodic pressure sensor signals from the second plurality of selected pressure sensor signals, determine a systolic blood pressure value and a diastolic blood pressure value.

A representative apparatus embodiment may further comprise: a housing coupled to the pressure sensor array and to the processor; and a wearable attachment coupled to the housing.

In a representative apparatus embodiment, the processor may be further adapted, for each periodic pressure sensor signal of the second plurality of selected pressure sensor signals, to determine a cross-coherence with each nearest neighbor pressure sensor signal; and select a periodic pressure sensor signal having a highest mean cross-coherence. For such a representative apparatus embodiment, the processor may be further adapted to determine the systolic blood pressure value as a maximum of the periodic pressure sensor signal having a highest mean cross-coherence; and determine the diastolic blood pressure value as a minimum of the periodic pressure sensor signal having a highest mean cross-coherence.

In a representative apparatus embodiment, the processor may be further adapted to determine the mean and standard deviation of the first plurality of selected pressure sensor signals.

In a representative apparatus embodiment, the processor may be further adapted to perform a first filtering of the plurality of pressure sensor signals to eliminate one or more pressure sensor signals below a selected or predetermined threshold.

A representative apparatus may further comprise: an analog-to-digital converter to sample and convert the plurality of pressure sensor signals into a corresponding plurality of digital amplitude values.

In a representative apparatus embodiment, the processor may be further adapted, using one or more periodic pressure sensor signals from the second plurality of selected pressure sensor signals, to determine a heart rate.

In a representative apparatus embodiment, the processor may be further adapted to perform a Kalman filtering of the second plurality of selected pressure sensor signals; determine the systolic blood pressure value as a maximum of the Kalman filter data; and determine the diastolic blood pressure value as a minimum of the Kalman filter data.

A representative apparatus may further comprise: a display for displaying the determined blood pressure value and other vital sign information to the user. A representative apparatus also may further comprise: a wireless transmitter to transmit the determined blood pressure value and other vital sign information to a central location. A representative apparatus also may further comprise: a network interface circuit to transmit the determined blood pressure value and other vital sign information to a central location. A representative apparatus also may further comprise: a memory circuit storing the determined blood pressure value and other vital sign information in a memory circuit.

A representative system embodiment is disclosed for determining a blood pressure of a subject human being for ambulatory monitoring, the representative system embodiment comprising: a wearable apparatus and a central monitor.

In such a representative system embodiment, the wearable apparatus may comprise: a pressure sensor array having a plurality of pressure sensors spaced-apart in at least two dimensions, the pressure sensor array generating a plurality of pressure sensor signals, one or more of the pressure sensor signals having data representing amplitudes of one or more arterial pressure waves; and a wireless transmitter coupled to the pressure sensor array to transmit the plurality of pressure sensor signals.

In such a representative system embodiment, the central monitor may comprise: a memory circuit; a wireless transceiver to receive the transmitted plurality of pressure sensor signals; and a processor coupled to the wireless transceiver and to the memory, the processor adapted to a processor coupled to the pressure sensor array, the processor adapted to determine a frequency content of each of the one or more of the pressure sensor signals having data; select one or more periodic pressure sensor signals to form a first plurality of selected pressure sensor signals; select one or more periodic pressure sensor signals within a selected or predetermined deviation, such as a standard deviation, of a mean of the first plurality of selected pressure sensor signals to form a second plurality of selected pressure sensor signals; and using one or more periodic pressure sensor signals from the second plurality of selected pressure sensor signals, determine a systolic blood pressure value and a diastolic blood pressure value.

In such a representative system embodiment, the wearable apparatus may further comprise: a housing coupled to the pressure sensor array; and a wearable attachment coupled to the housing.

In a representative system embodiment, the processor may be further adapted, for each periodic pressure sensor signal of the second plurality of selected pressure sensor signals, to determine a cross-coherence with each nearest neighbor pressure sensor signal; and select a periodic pressure sensor signal having a highest mean cross-coherence. In such a representative system embodiment, the processor may be further adapted to determine the systolic blood pressure value as a maximum of the periodic pressure sensor signal having a highest mean cross-coherence; and determine the diastolic blood pressure value as a minimum of the periodic pressure sensor signal having a highest mean cross-coherence.

In a representative system embodiment, the processor may be further adapted to determine the mean and standard deviation of the first plurality of selected pressure sensor signals.

In a representative system embodiment, the processor may be further adapted to perform a first filtering of the plurality of pressure sensor signals to eliminate one or more pressure sensor signals below a selected or predetermined threshold.

In such a representative system embodiment, the wearable apparatus may further comprise: an analog-to-digital converter to sample and convert the plurality of pressure sensor signals into a corresponding plurality of digital amplitude values.

In a representative system embodiment, the processor may be further adapted, using one or more periodic pressure sensor signals from the second plurality of selected pressure sensor signals, to determine a heart rate.

In a representative system embodiment, the processor may be further adapted to perform a Kalman filtering of the second plurality of selected pressure sensor signals; determine the systolic blood pressure value as a maximum of the Kalman filter data; and determine the diastolic blood pressure value as a minimum of the Kalman filter data.

In a representative system embodiment, the wearable apparatus may further comprise: a display for displaying the determined blood pressure value and other vital sign information to the user.

In a representative system embodiment, the wireless transceiver is configured to transmit the determined blood pressure value and other vital sign information to a central location.

In a representative system embodiment, the central monitor may further comprise: a network interface circuit to transmit the determined blood pressure value and other vital sign information to a central location.

In a representative system embodiment, the memory circuit may also store the determined blood pressure value and other vital sign information.

Another representative method embodiment for determining a blood pressure of a subject human being for ambulatory monitoring is disclosed, with the representative method comprising: using a pressure sensor array having a plurality of pressure sensors spaced-apart in at least two dimensions, applanating an artery; receiving a plurality of pressure sensor signals, one or more of the pressure sensor signals having data representing amplitudes of one or more arterial pressure waves; filtering the plurality of pressure sensor signals to eliminate one or more pressure sensor signals below a selected or predetermined threshold; performing a Fourier transformation to determine a frequency content of each of the one or more of the pressure sensor signals having data; selecting one or more periodic pressure sensor signals to form a first plurality of selected pressure sensor signals, the one or more periodic pressure sensor signals having a frequency between 0.5 to 3.5 Hz; determining the mean and standard deviation of the first plurality of selected pressure sensor signals; selecting one or more periodic pressure sensor signals within a selected or predetermined deviation, such as a standard deviation, of the mean of the first plurality of selected pressure sensor signals to form a second plurality of selected pressure sensor signals; for each periodic pressure sensor signal of the second plurality of selected pressure sensor signals, determining a cross-coherence with each nearest neighbor pressure sensor signal; selecting a periodic pressure sensor signal having a highest mean cross-coherence; determining a systolic blood pressure value as a maximum of the periodic pressure sensor signal having a highest mean cross-coherence; determining a diastolic blood pressure value as a minimum of the periodic pressure sensor signal having a highest mean cross-coherence; and displaying the determined blood pressure value and other vital sign information to the user.

Another representative apparatus embodiment is disclosed for determining a blood pressure of a subject human being for ambulatory monitoring, the representative apparatus embodiment comprising: a display; a memory; a pressure sensor array having a plurality of pressure sensors spaced-apart in at least two dimensions; and a processor coupled to the pressure sensor array, to the display and to the memory, the processor adapted to receive a plurality of pressure sensor signals, one or more of the pressure sensor signals having data representing amplitudes of one or more arterial pressure waves; filtering the plurality of pressure sensor signals to eliminate one or more pressure sensor signals below a selected or predetermined threshold; perform a Fourier transformation to determine a frequency content of each of the one or more of the pressure sensor signals having data; select one or more periodic pressure sensor signals to form a first plurality of selected pressure sensor signals, the one or more periodic pressure sensor signals having a frequency between 0.5 to 3.5 Hz; determine the mean and standard deviation of the first plurality of selected pressure sensor signals; select one or more periodic pressure sensor signals within a selected or predetermined deviation, such as a standard deviation, of the mean of the first plurality of selected pressure sensor signals to form a second plurality of selected pressure sensor signals; for each periodic pressure sensor signal of the second plurality of selected pressure sensor signals, determine a cross-coherence with each nearest neighbor pressure sensor signal; select a periodic pressure sensor signal having a highest mean cross-coherence; determine a systolic blood pressure value as a maximum of the periodic pressure sensor signal having a highest mean cross-coherence; determine a diastolic blood pressure value as a minimum of the periodic pressure sensor signal having a highest mean cross-coherence; and provide the systolic blood pressure value and the diastolic blood pressure value to the display.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which.

DETAILED DESCRIPTION OF REPRESENTATIVE EMBODIMENTS

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

As mentioned above and as discussed in greater detail below, the representative apparatus, system and method provide for noninvasive, ambulatory blood pressure and other vital sign monitoring. Other vital signs may also be determined, including without limitation heart rate, cardiac output, and stroke volume.

Figure 1:
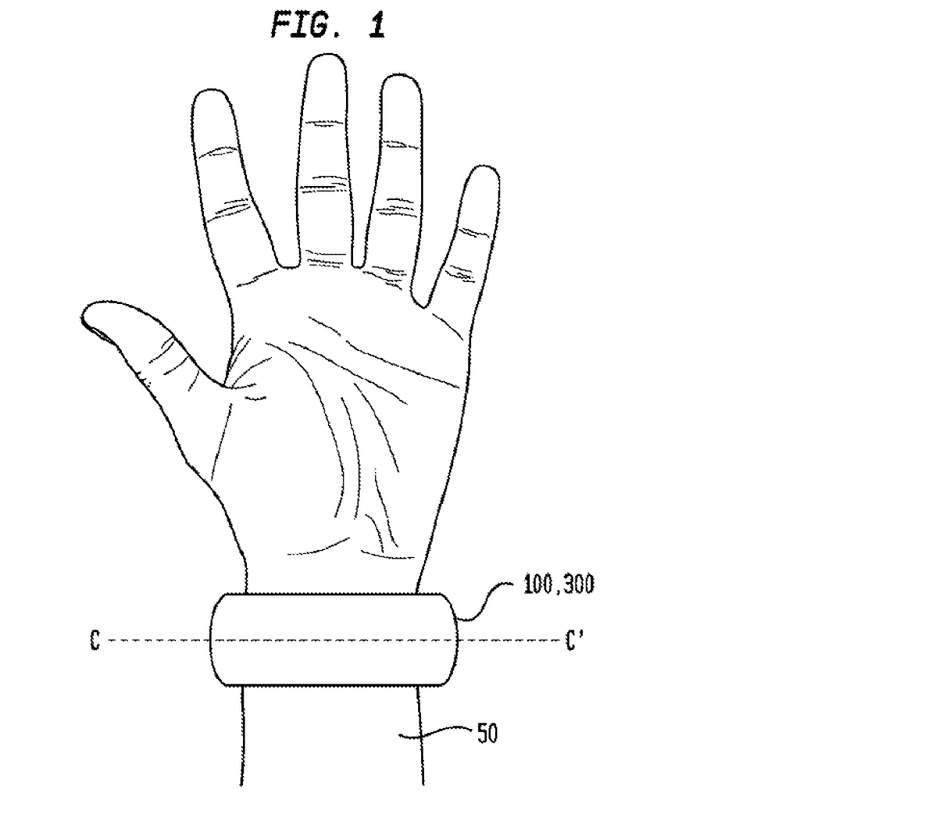
FIG. 1 is a plan view diagram illustrating representative first and/or second apparatus embodiments with a wearable wristband attachment attached to a wrist of an individual subject.
Figure 2:
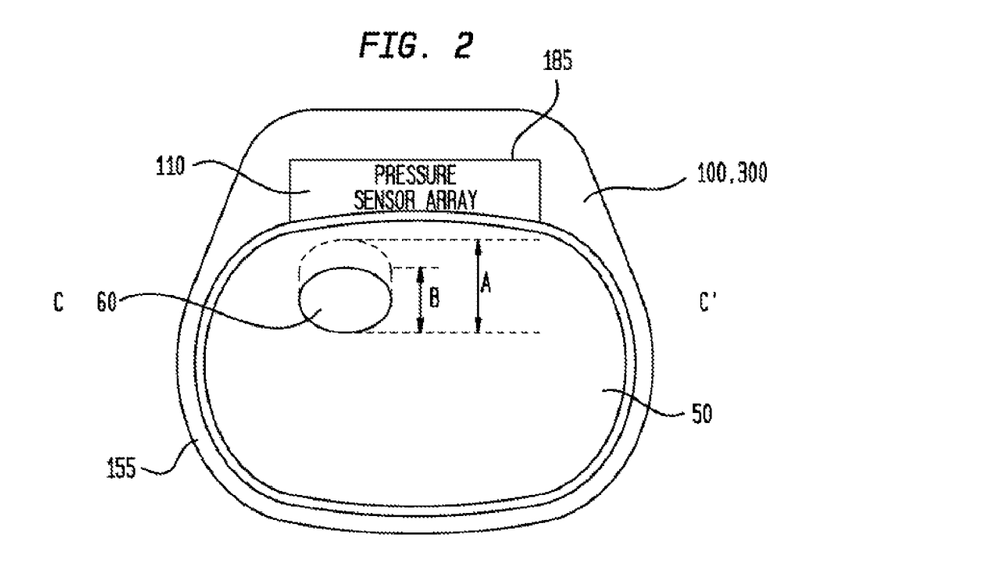
FIG. 2 is a cross-sectional view diagram illustrating representative first and/or second apparatus embodiments with a wearable wristband attachment attached to a wrist of an individual subject of FIG. 1 with applanation of a radial artery.
Figure 3:
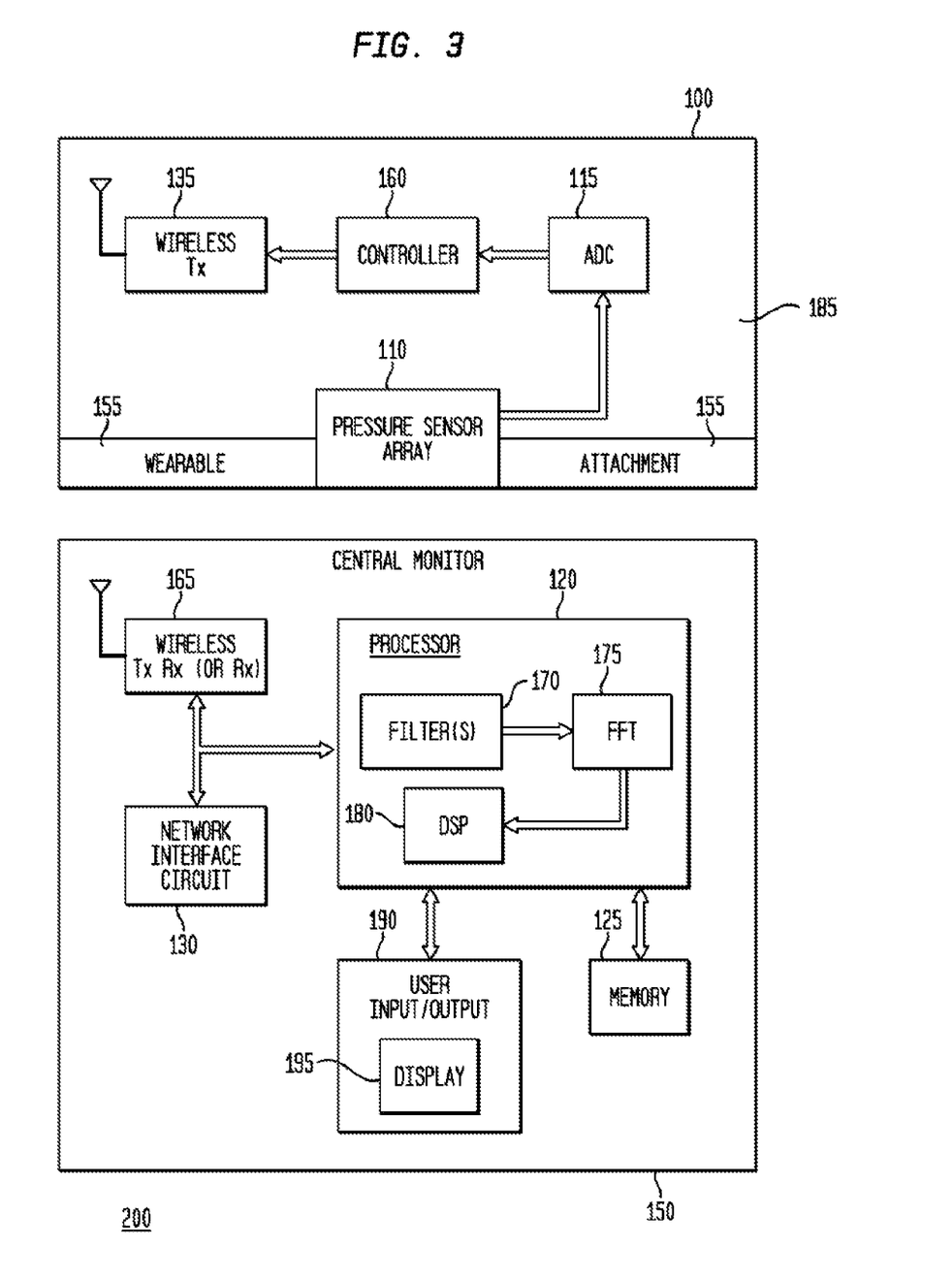
FIG. 3 is a block diagram of representative first apparatus and first system embodiments.
Figure 4:
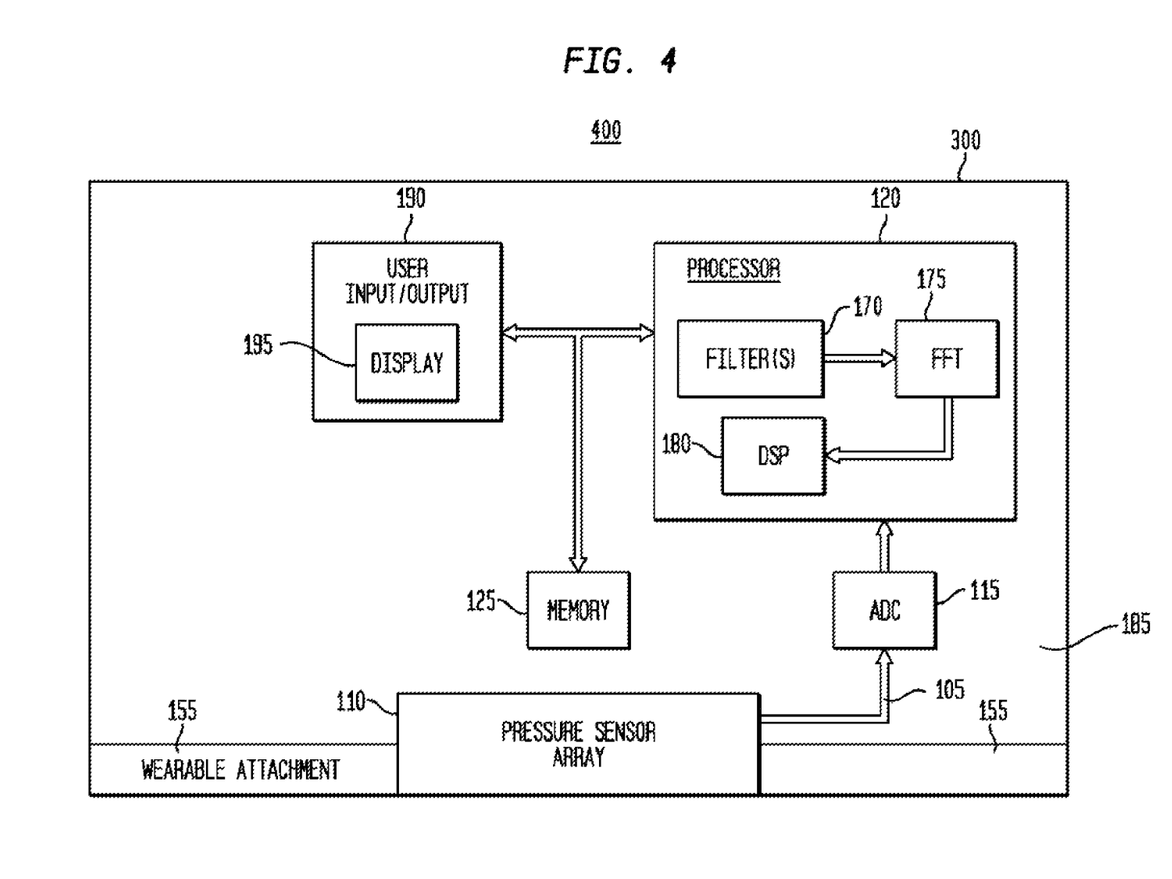
FIG. 4 is a block diagram of representative second apparatus and second system embodiments.
Figure 5:
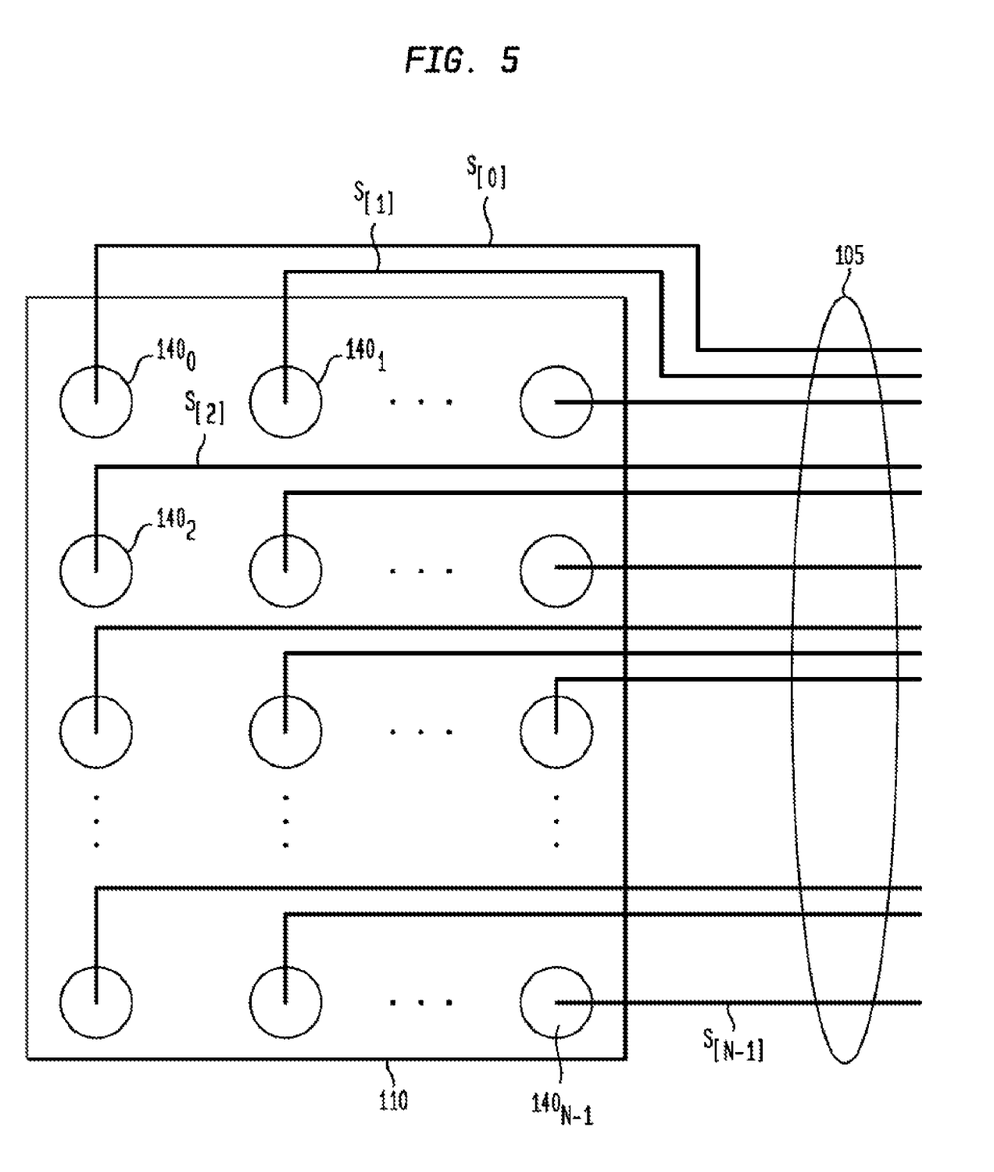
FIG. 5 is a block diagram of a representative pressure sensor array.

FIG. 1 is a plan view diagram illustrating representative first and/or second apparatus 100, 300 embodiments with a wearable wristband attachment attached to a wrist 50 of an individual subject. FIG. 2 is a cross-sectional view (through the C-C' plane) illustrating representative first and/or second apparatus 100, 300 embodiments with a wearable wristband attachment attached to a wrist 50 of an individual subject of FIG. 1 with applanation of a radial artery 60. FIG. 3 is a block diagram of representative first apparatus 100 and first system 200 embodiments. FIG. 4 is a block diagram of representative second apparatus 300 and second system 400 embodiments. FIG. 5 is a block diagram of a representative pressure sensor array 110.

As illustrated in FIGS. 1 and 2, the representative first and/or second apparatus 100, 300 embodiments provide a predetermined or potentially variable amount of pressure to the wrist 50 of an individual subject to applanate the artery 60, slightly flattening the artery (from a generally more circular cross-section, illustrated using dashed lines) and generally decreasing its diameter from "A" to a smaller diameter "B", but without occluding the artery. With such applanation, one or more pressure sensors 140 of the pressure sensor array 110 of the representative first and/or second apparatus 100, 300 embodiments is arranged or positioned substantially over the artery 60 to detect and/or measure pressure from the applanated artery 60 and the surrounding tissue. More specifically, one or more pressure sensors 140 the pressure sensor array 110 will generally be positioned substantially over the flattened portion of the applanated artery 60, so that the entire area of the one or more pressure sensors 140 is arranged substantially over the flattened portion of the applanated artery 60 for accurate pressure measurements, while other pressure sensors 140 of the pressure sensor array 110 may be positioned medially or laterally from the applanated artery 60.

FIG. 3 is a block diagram of representative first apparatus 100 and first system 200 embodiments. As illustrated in FIG. 3, a first apparatus 100 is utilized in the first system 200 to acquire pressure measurements or data, from locations or positions over an artery in the neck, lower or upper extremities, or other accessible regions of the individual, utilized in BP measurements or determinations, such as positioned over the radial artery 60 as discussed above. The first system 200 further comprises a central monitor 150, which receives the pressure measurements or data from the first apparatus 100, performs signal and data processing, and generates corresponding estimates or measurements of blood pressure and other vital signs, as mentioned above.

It should be noted that the central monitor 150 is "central" in the sense of being the main, predominant or principal receivers of the signals from the apparatus 100, and the provider of corresponding estimates of measurements of blood pressure and other vital signs, and not "central" in terms of determining a "central blood pressure".

The first apparatus 100 comprises a pressure sensor array 110, an analog-to-digital converter (ADC) 115, and a wireless transmitter 135. The pressure sensor array 110 comprises a plurality of spaced-apart pressure sensors 140 arranged or disposed in an array (as illustrated in FIG. 5), each of which senses pressure (as a force transducer having a corresponding area), and generates a corresponding pressure sensor 140 signal which is indicative of an arterial pressure when positioned over an artery. The pressure sensor array 110, an analog-to-digital converter (ADC) 115, and a wireless transmitter 135 are typically arranged or disposed within a housing 185. The corresponding pressure sensor 140 signal may be an analog pressure sensor (electrical)

signal, and if so, the analog-to-digital converter (ADC) 115 samples the analog pressure sensor signals from each of the pressure sensors 140 of the pressure sensor array 110 and generates a stream or series of corresponding digital amplitude values, each of which is indicative of or represents the amplitude of one or more arterial pressure waves occurring during the sampling time interval. Alternatively, the corresponding pressure sensor 140 signal may be provided as a digital amplitude value, also which is indicative of or represents the amplitude of one or more arterial pressure waves occurring during the sampling time interval, and in which case, the analog-to-digital converter (ADC) 115 may be omitted as a separate component in the first and/or second apparatus 100, 300. The wireless transmitter 135 wirelessly transmits the corresponding stream or series of corresponding digital amplitude values to the central monitor 150.

Optionally, the first apparatus 100 may also include a controller 160 and a wearable attachment 155. When included, the wearable attachment 155 may be a wristband, an adhesive patch, a band for an upper or lower part of an arm or leg, or a ring for a finger, all for example and without limitation. In other embodiments which do not include a wearable attachment 155, the housing 185 may have any suitable form factor, e.g., as any type of portable device, such as a handheld device, and optionally may also include one or more components of the central monitor 150, also for example and without limitation. Other types of sensors may also be included in the first and/or second apparatus 100, 300. When a controller 160 is included, the controller 160 combines the stream or series of corresponding digital values (indicative of the arterial pressure waves), from each pressure sensor 140 of the pressure sensor array 110, along with any other sensor data, for wireless transmission by the wireless transmitter 135 to the central monitor 150.

The central monitor 150 generally comprises a wireless transceiver (or receiver with or without a transmitter) 165, a processor 120, a memory 125, a network interface circuit 130, and a user input and output device 190, such as a touch screen display 195 or any other type of visual display, for example. The memory 125 generally stores calibration data, as discussed in greater detail below, such as for any offset or scaling, and may also store collected data and corresponding results, such as pressure measurements or determinations and corresponding estimates or measurements of the BP and other vital signs of the individual. The wireless transceiver 165, which may be included in the network interface circuit 130, receives the stream or series of corresponding digital amplitude values indicative of or representing the arterial pressure waves, from the first apparatus 100, and provides or transfers this data to the processor 120. Using this stream or series of corresponding digital amplitude values (indicative of or representing the arterial pressure waves), the processor 120 generates the pressure measurements or determinations and corresponding estimates or measurements of the BP and other vital signs of the individual. As discussed in greater detail below with reference to the flow charts of FIGS. 6 and 7, the processor 120 may also be considered to include, such as through configuration or programming, one or more filters 170, a fast Fourier transform (or discrete Fourier transform) circuit or block 175, and a digital signal processor ("DSP") or DSP block 180.

The processor 120 may then provide the estimates or measurements of the BP and other vital signs of the individual to the user input and output device 190, such as for display to the individual on a touch screen display 195. The processor 120 also may then provide the estimates or measurements of the BP and other vital signs of the individual to the network interface circuit 130, such as for transmission of the estimates or measurements of the BP and other vital signs of the individual to another location or device, such as to a hospital or clinic computing system, also for example and without limitation.

Not separately illustrated in FIG. 3, those having skill in the art will recognize that devices such as central monitor 150 and first apparatus 100 also generally include clocking circuitry and distribution, and a power supply with power distribution, which may be a battery or other energy source, for example and without limitation.

It should be noted that various features and physiological changes or aspects of an individual and/or the arteries of an individual, such as skin and vessel elasticity or stiffness, the movement of the individual, and potentially also the contact pressure exerted by the first apparatus 100 (and/or second apparatus 300) on the subject individual, may also affect the measurement of the amplitude of the arterial pressure waves and resulting pressure measurements or determinations, without corresponding changes in the subject's absolute BP. These pressures may be measured or otherwise determined, such as during a calibration process, and utilized to provide offsets and/or scaling of the measured BP magnitudes, discussed in greater detail below with reference to FIGS. 6 and 7.

Referring to FIG. 4, a second system 400 generally comprises a second apparatus 300, and any central monitor 150 is merely optional. As illustrated in FIG. 4, a second apparatus 300 is utilized in the second system 400 to acquire pressure measurements or data, from locations or positions over an artery in the neck, lower or upper extremities, or other accessible regions of the individual, utilized in BP measurements or determinations, such as positioned over the radial artery 60 as discussed above. For example and without limitation, in a second system 400, a second apparatus 300 may be worn on a left or right wrist. The second apparatus 300 operates as described above for the first apparatus 100 and further comprises many of the components and functionality of a central monitor 150. Accordingly, the second apparatus 300 also performs signal and data processing, and generates corresponding estimates or measurements of blood pressure and other vital signs, as mentioned above, as discussed above.

The second system 400 may be viewed as combining the components and functionality of many (but generally not all) the components and functions of the first system 200 into one device (as a second apparatus 300), rather than distributing these components and functions between and among two devices (a first apparatus 100 and a central monitor 150). The second system 400 also eliminates components that could now be considered redundant, optional or unnecessary when selected components and functions of the central monitor 150 are included in the second apparatus 300 (e.g., eliminating a controller 160 and wireless transmitter 135 in the second apparatus 300, and optionally eliminating a wireless transceiver 165 and/or a network interface circuit 130 of a central monitor 150). Accordingly, unless specified to the contrary, the components of the second system 400 generally function identically to the components of the first system 200 described above, and with the second apparatus 300 generally including or combining the overall functionality of a first apparatus 100 and a central monitor 150, without redundancy.

The second apparatus 300 also comprises a pressure sensor array 110 having one or more pressure sensors 140, and generally also an analog-to-digital converter (ADC) 115, all of which function as discussed above. Optionally, the second apparatus 300 may also include other sensors (not separately illustrated), and a wearable attachment 155, all of which function as discussed above, with the various components arranged or disposed within a housing 185.

The second apparatus 300 also generally comprises a processor 120, a memory 125, and a user input and output device 190, such as a touch screen display 195 or any other type of visual display, an on/off button, and so on, also for example, all of which function as discussed above. Optionally, the second apparatus 300 may include a network interface circuit 130. The memory 125 of the second apparatus 300 also generally stores calibration data, as discussed in greater detail below, and may also store collected data and corresponding results, such as measurements or determinations of the BP and other vital signs of the individual. Optionally, the second apparatus 300 may include a wireless transceiver 165. The digital amplitude values indicative of or representing the arterial pressure waves generated by the analog-to-digital converter (ADC) 115, from the corresponding analog sensor electrical signal provided by corresponding pressure sensors 140 of the pressure sensor array 110, or directly from the pressure sensors 140 of the pressure sensor array 110, are also transferred to the processor 120 of the second apparatus 300. Using this stream or series of corresponding digital amplitude values (indicative of or representing the arterial pressure waves, along with any other data (including calibration data, if any), the processor 120 of the second apparatus 300 also generates the BP measurements or determinations and other vital signs of the individual, as discussed above. Also as discussed in greater detail below with reference to the flow charts of FIGS. 6 and 7, the processor 120 may also be considered to include, such as through configuration or programming, one or more filters 170, a fast Fourier transform (or discrete Fourier transform) circuit or block 175, and a digital signal processor ("DSP") or DSP block 180.

The processor 120 may then provide the estimates or measurements of the BP and other vital signs of the individual to the user input and output device 190 of the second apparatus 300, such as for display to the individual on a touch screen or other display 195. For example, in a representative embodiment in which the second apparatus 300 is worn on a left or right wrist by a subject individual, using a wristband or bracelet as a wearable attachment 155, the individual's BP and other vital signs may be displayed and viewed by the user in real time similarly or equivalently to reading a wristwatch. Also not separately illustrated in FIG. 4, those having skill in the art will recognize that devices such as the first apparatus 100 and second apparatus 300 also generally include clocking circuitry and distribution, and a power supply with power distribution, which may be a battery or other energy source, for example and without limitation.

It should be noted that any of the systems 200, 400 may be utilized in conjunction with other devices and systems, as known in the computer and communications fields, such as optional relay stations or docking units, not separately illustrated. For example and without limitation, such an optional relay station or docking unit may receive BP measurements or determinations from a second apparatus 300, and transfer this data to a network or cloud storage device (also not separately illustrated), which also may be accessed by physicians or other clinical staff, such as through a compatible portal at a hospital or a clinical computing system.

Referring to FIG. 5, a pressure sensor array 110 comprises a plurality of spaced-apart pressure sensors 140, arranged or positioned as a regularly spaced array. As illustrated in FIG. 5, a plurality of "N" pressure sensors 140 are utilized, each of which generates a corresponding pressure sensor 140 signal, illustrated as pressure sensor 140 signals S[0], S[1], S[2], through S[N−1], output on bus or wires 105 to the ADC 115 (or directly to the controller 160 or wireless transmitter 135 for a first apparatus 100 or directly to a processor 120 for a second apparatus 300), which may be analog or digital, as discussed above. In a representative embodiment, the number "N" of pressure sensors 140 may be in the hundreds to thousands to create a comparatively dense pressure sensor array 110, such as an array of 24×24 pressure sensors 140 (576 pressure sensors 140), or an array of 64×64 pressure sensors 140 (4096 pressure sensors 140), or an array of 130×130 pressure sensors 140 (16,900 pressure sensors 140), for example and without limitation. It should be noted that the pressure sensor array 110 does not need to be symmetric, e.g., an array of A×B pressure sensors 140 may be utilized, such an array of 100×50 pressure sensors 140 (5000 pressure sensors 140), also for example and without limitation.

Figure 6A:
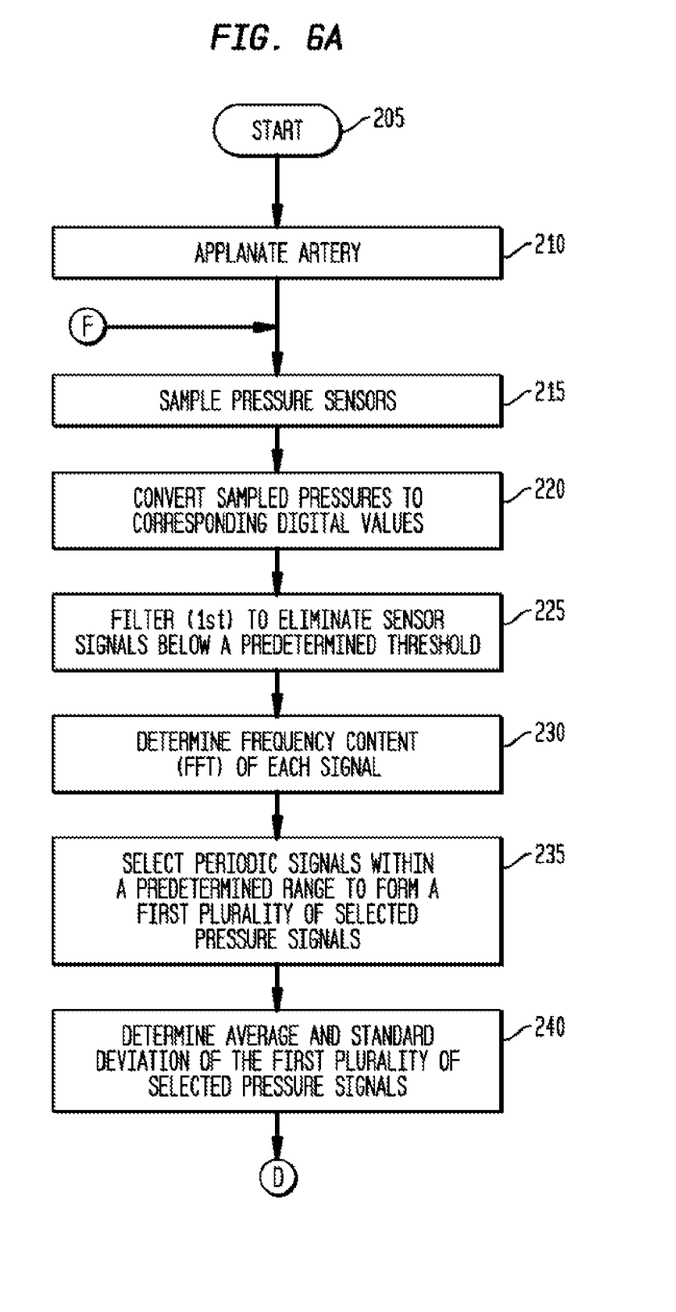
FIGS. 6A, 6B and 6C (collectively referred to as FIG. 6) is a flow chart of a representative first method embodiment for the determination of systolic and diastolic blood pressure values, heart rate and other vital signs.
Figure 6B:
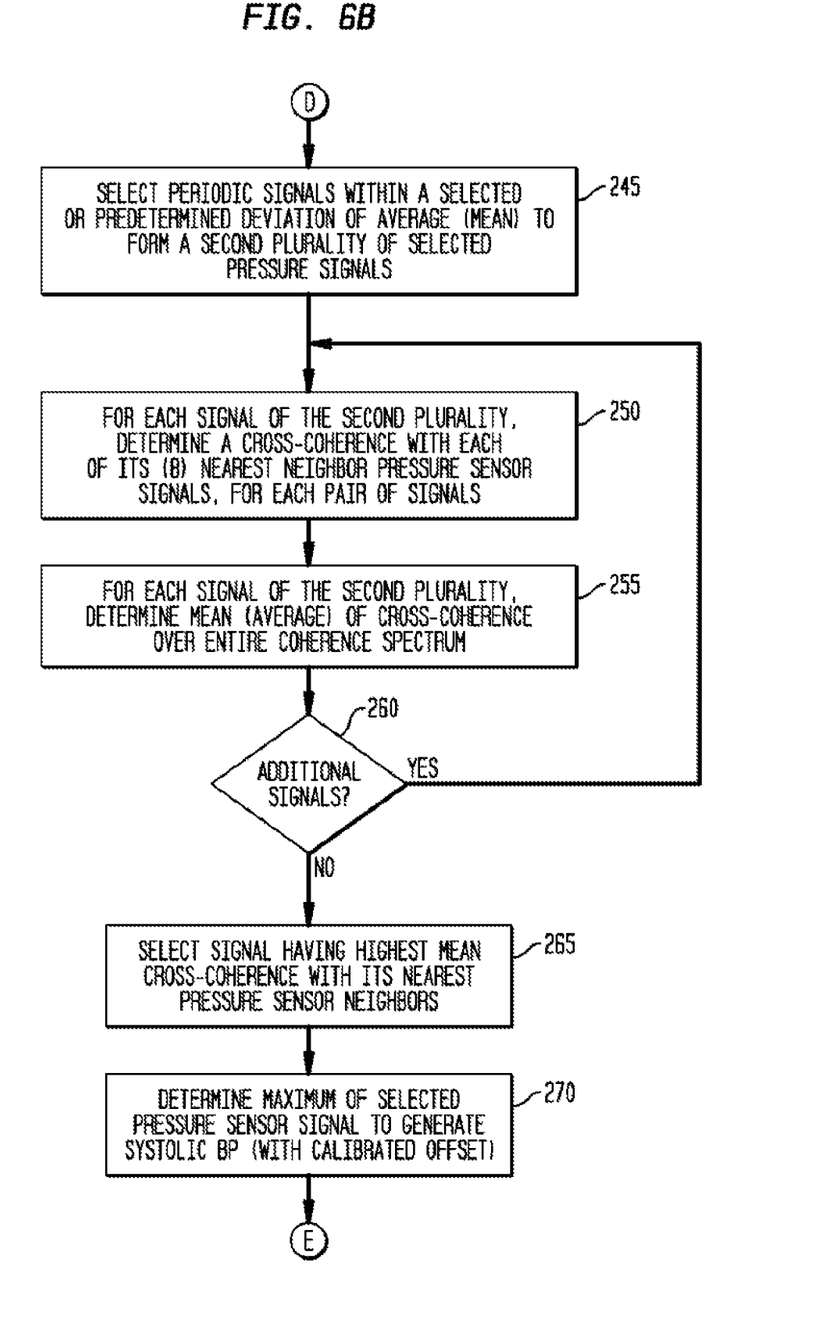
Figure 6C:
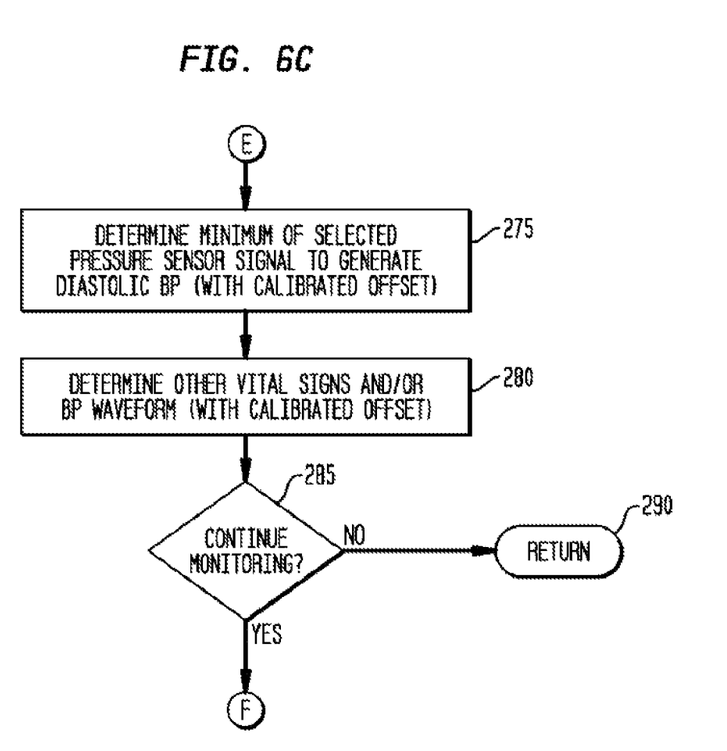

FIG. 6 is a flow chart of a representative first method embodiment for the determination of systolic and diastolic blood pressure values, heart rate and other vital signs. Beginning with start step 205, an artery is applanated, step 210, such as by applying the pressure sensor array 110 against a wrist 50 and applying some pressure, which generally will applanate a radial artery 60, for example. As each of the pressure sensors 140 generate a corresponding pressure sensor 140 signal, the pressure sensor 140 signals are sampled, step 215, and converted to corresponding digital amplitude values (indicative of or representing the arterial pressure waves), step 220, such as using an ADC 115, which are provided to the processor 120 in a system 200, 400, such as through the wireless transmitter 135 or directly from the ADC 115.

Many of the pressure sensors 140 of the pressure sensor array 110, however, will not be positioned over the applanated artery and will not be generating any pressure measurements or will be generating pressure measurements below a selected or predetermined threshold. According, using one or more filters 170, the processor 120 performs a first filtering, step 225, eliminating pressure sensor 140 signals below a selected or predetermined threshold, such as those which are not generating data (i.e., have a zero value) from further signal processing. The processor 120 determines the frequency content of each pressure sensor 140 signal above the selected or predetermined threshold, such as those having data (a non-zero value), step 230, such as by performing a fast Fourier transformation ("FFT") using FFT block 175. Using the frequency content, in step 235, the processor 120 selects those pressure sensor 140 signals which are periodic within a predetermined range to form a first plurality of selected pressure sensor 140 signals (e.g., having the most common or dominant frequency), such as those pressure sensor 140 signals which have a frequency in the range of 0.5 to 3.5 Hz, which would correspond to a heart rate of 30-210 beats/minute.

The processor 120 then determines the mean (average) and standard deviation of the first plurality of selected pressure sensor 140 signals, step 240, such as using DSP block 180, and selects those pressure sensor 140 signals from the first plurality of selected pressure sensor 140 signals which are within a selected or predetermined deviation, such as a standard deviation, of the mean, step 245, to form a second plurality of selected pressure sensor 140 signals, also typically using DSP block 180.

For each pressure sensor 140 signal of the second plurality of selected pressure sensor 140 signals, in step 250, the processor 120 determines a cross-coherence of the pressure sensor 140 signal with each pressure sensor 140 signal of its nearest neighbor pressure sensors, typically pair-wise with each pressure sensor 140 signal of eight possible nearest pressure sensor 140 neighbors of the pressure sensor array 110. For each pressure sensor 140 signal of the second plurality of selected pressure sensor 140 signals, in step 255, the processor 120 determines the mean (average) of the cross-coherence of the pressure sensor 140 signal with each pressure sensor 140 signal of its nearest neighbor pressure sensor 140 signals, across the entire coherence spectrum. When there are additional pressure sensor 140 signals of the second plurality of selected pressure sensor 140 signals, step 260, the method iterates, continuing to perform steps 250 and 255 for the additional pressure sensor 140 signals.

When all of the cross-coherence determinations of steps 250 and 255 have been made, following step 260, the processor 120 selects a pressure sensor 140 signal having the highest (largest or greatest) cross-coherence with the pressure sensor 140 signals of its nearest pressure sensor 140 neighbors, step 265, e.g., highest average magnitude-squared coherence spectrum. This may also include selecting a pressure sensor 140 signal having a certain or selected pattern. The selected pressure sensor 140 signal having the highest cross-coherence then has a high (or higher) likelihood of being properly positioned over the applanated artery 60 and of properly or accurately detecting the corresponding pressures of the arterial pressure waves. The processor 120 then determines the maximum value from the data of the selected pressure sensor 140 signal having the highest cross-coherence, step 270, which corresponds to or generates the systolic BP measurement or determination, or which may also include a calibrated offset or scaling factor. The processor 120 then determines the minimum value from the data of the selected pressure sensor 140 signal having the highest cross-coherence, step 275, which corresponds to or generates the diastolic BP measurement or determination, or which may also include a calibrated offset or scaling factor. Other vital signs, such as heart rate and stroke volume, or the entire BP waveform (with any calibrated offset or scaling), may also be determined by the processor 120, step 280.

When monitoring is to continue, step 285, the method iterates, returning to step 215, and otherwise, the method may end, return step 290. Alternatively, as the pressure sensors 140 may be generating pressure sensor 140 signals which are continually sampled and converted to corresponding digital amplitude values (indicative of or representing the arterial pressure waves), the method may iterate and return to step 225, shifting a time window for examining the incoming digital data values.

Figure 7A:
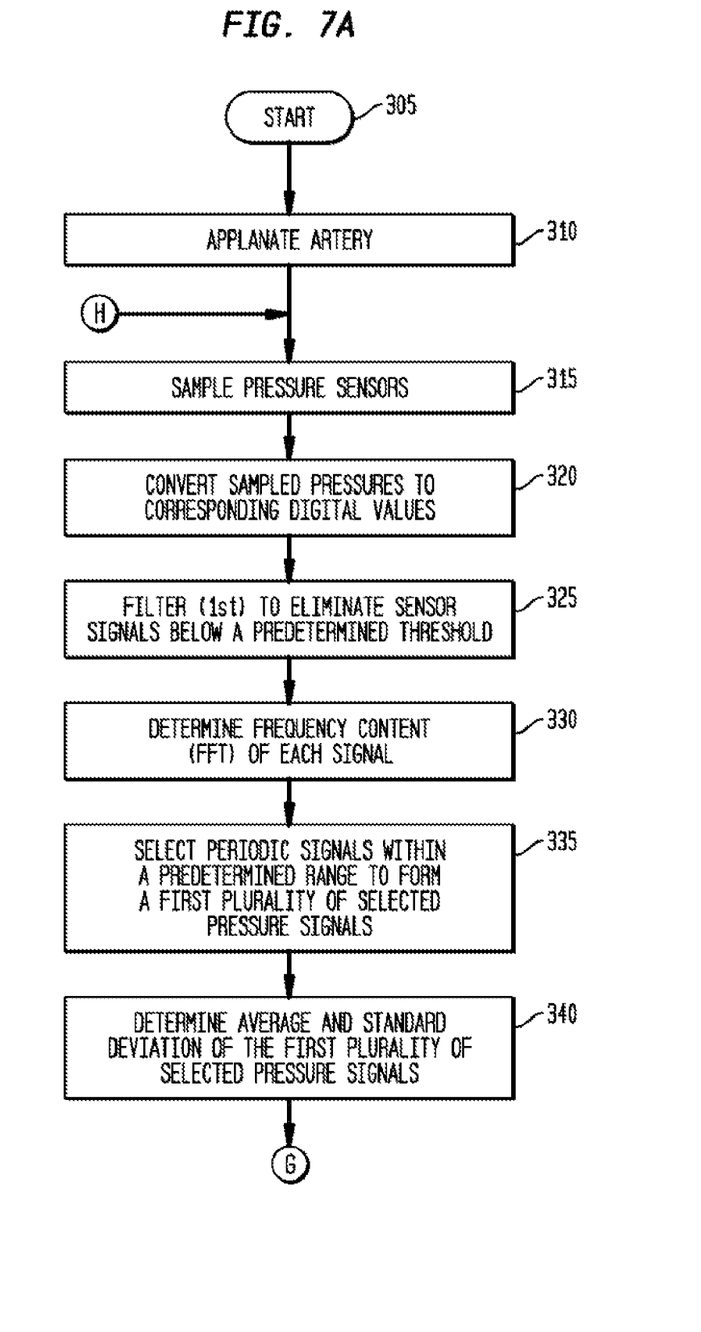
FIGS. 7A and 7B (collectively referred to as FIG. 7) is a flow chart of a representative second method embodiment for the determination of systolic and diastolic blood pressure values, heart rate and other vital signs.
Figure 7B:
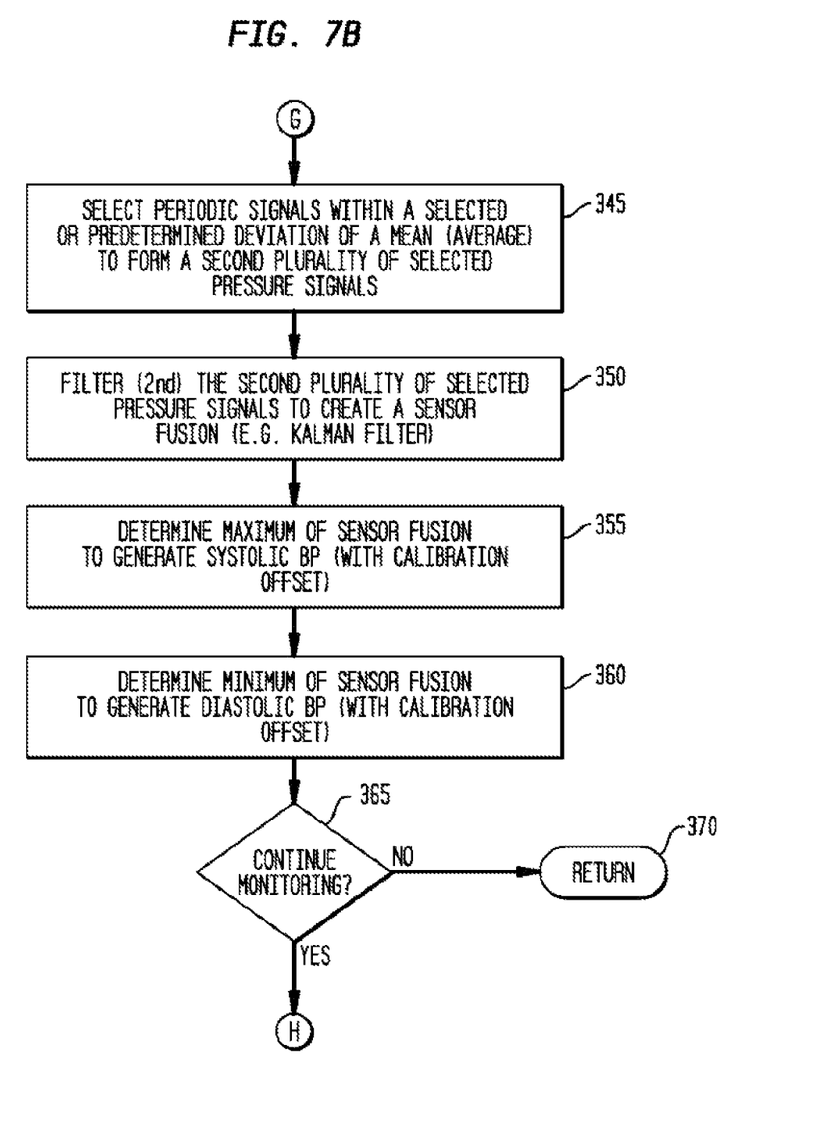

FIG. 7 is a flow chart of a representative second method embodiment for the determination of systolic and diastolic blood pressure values, heart rate and other vital signs. For the second method, steps 305-345 correspond to steps 205-245 of the first method. Beginning with start step 305, an artery is applanated, step 310, such as by applying the pressure sensor array 110 against a wrist 50 and applying some pressure, which generally will applanate a radial artery 60, for example. As each of the pressure sensors 140 generate a corresponding pressure sensor 140 signal, the pressure sensor 140 signals are sampled, step 315, and converted to corresponding digital amplitude values (indicative of or representing the arterial pressure waves), step 320, such as using an ADC 115, which are provided to the processor 120 in a system 200, 400, such as through the wireless transmitter 135 or directly from the ADC 115.

Many of the pressure sensors 140 of the pressure sensor array 110, however, also will not be positioned over the applanated artery and will not be generating any pressure measurements or will be generating pressure measurements below a selected or predetermined threshold, as discussed above. According, using one or more filters 170, the processor 120 performs a first filtering, step 325, eliminating pressure sensor 140 signals below a selected or predetermined threshold, such as those which are not generating data (i.e., have a zero value) from further signal processing. The processor 120 also determines the frequency content of each pressure sensor 140 signal above the selected or predetermined threshold, such as those having data (a non-zero value), step 330, such as by performing a fast Fourier transformation ("FFT") using FFT block 175. Using the frequency content, in step 335, the processor 120 selects those pressure sensor 140 signals which are periodic within a predetermined range to form a first plurality of selected pressure sensor 140 signals (e.g., having the most common or dominant frequency), such as those pressure sensor 140 signals which have a frequency in the range of 0.5 to 3.5 Hz, as mentioned above, which would correspond to a heart rate of 30-210 beats/minute.

The processor 120 then determines the mean (average) and standard deviation of the first plurality of selected pressure sensor 140 signals, step 340, such as using DSP block 180, and selects those pressure sensor 140 signals from the first plurality of selected pressure sensor 140 signals which are within a selected or predetermined deviation, such as a standard deviation, of the mean, step 345, to form a second plurality of selected pressure sensor 140 signals, also typically using DSP block 180.

For the second method, the processor 120 then performs a second filtering step of the second plurality of selected pressure sensor 140 signals, such as performing Kalman filtering to create a "sensor fusion", step 350, or utilizing one or more Hidden Markov Models, for example and without limitation. Following the second filtering, the processor 120 then determines the maximum value from the data of the second filtering, step 355, which corresponds to or generates the systolic BP measurement or determination, or which may also include a calibrated offset or scaling factor. The processor 120 also then determines the minimum value from the data of the second filtering, step 360, which corresponds to or generates the diastolic BP measurement or determination, or which may also include a calibrated offset or scaling factor.

When monitoring is to continue, step 365, the method iterates, returning to step 315, and otherwise, the method may end, return step 370. Alternatively, as the pressure sensors 140 may be generating pressure sensor 140 signals which are continually sampled and converted to corresponding digital amplitude values (indicative of or representing the arterial pressure waves), the method may iterate and return to step 325, also shifting a time window for examining the incoming digital data values.

It should be noted that additional filtering may be performed for either or both the first and/or second methods, such as to reduce or eliminate noise in any of the pressure sensor signals.

As used herein, a "processor" 120 or "controller" 160 may be any type of controller or processor, and may be embodied as one or more processor(s) 120 or controller(s) 160, configured, designed, programmed or otherwise adapted to perform the functionality discussed herein. As the term controller or processor is used herein, a processor 120 or controller 160 may include use of a single integrated circuit ("IC"), or may include use of a plurality of integrated circuits or other components connected, arranged or grouped together, such as controllers, microprocessors, digital signal processors ("DSPs"), array processors, graphics or image processors, parallel processors, multiple core processors, custom ICs, application specific integrated circuits ("ASICs"), field programmable gate arrays ("FPGAs"), adaptive computing ICs, associated memory (such as RAM, DRAM and ROM), and other ICs and components, whether analog or digital. As a consequence, as used herein, the term processor (or controller) should be understood to equivalently mean and include a single IC, or arrangement of custom ICs, ASICs, processors, microprocessors, controllers, FPGAs, adaptive computing ICs, or some other grouping of integrated circuits which perform the functions discussed below, with associated memory, such as microprocessor memory or additional RAM, DRAM, SDRAM, SRAM, MRAM, ROM, FLASH, EPROM or $E^2$PROM. A processor 120 or controller 160, with associated memory, may be adapted or configured (via programming, FPGA interconnection, or hard-wiring) to perform the methodology of the invention, as discussed herein. For example, the methodology may be programmed and stored, in a processor 120 or controller 160 with its associated memory (and/or memory 125) and other equivalent components, as a set of program instructions or other code (or equivalent configuration or other program) for subsequent execution when the processor or controller is operative (i.e., powered on and functioning). Equivalently, when the processor 120 or controller 160 may implemented in whole or part as FPGAs, custom ICs and/or ASICs, the FPGAs, custom ICs or ASICs also may be designed, configured and/or hard-wired to implement the methodology of the invention. For example, the processor 120 or controller 160 may be implemented as an arrangement of analog and/or digital circuits, controllers, microprocessors, DSPs and/or ASICs, collectively referred to as a "processor" or "controller", which are respectively hard-wired, programmed, designed, adapted or configured to implement the methodology of the invention, including possibly in conjunction with a memory 125.

The memory 125, which may include a data repository (or database), may be embodied in any number of forms, including within any computer or other machine-readable data storage medium, memory device or other storage or communication device for storage or communication of information, currently known or which becomes available in the future, including, but not limited to, a memory integrated circuit ("IC"), or memory portion of an integrated circuit (such as the resident memory within a processor 120, controller 160 or processor IC), whether volatile or non-volatile, whether removable or non-removable, including without limitation RAM, FLASH, DRAM, SDRAM, SRAM, MRAM, FeRAM, ROM, EPROM or $E^2$PROM, or any other form of memory device, such as a magnetic hard drive, an optical drive, a magnetic disk or tape drive, a hard disk drive, other machine-readable storage or memory media such as a floppy disk, a CDROM, a CD-RW, digital versatile disk (DVD) or other optical memory, or any other type of memory, storage medium, or data storage apparatus or circuit, which is known or which becomes known, depending upon the selected embodiment. The memory 125 may be adapted to store various look up tables, parameters, coefficients, other information and data, programs or instructions (of the software of the present invention), and other types of tables such as database tables.

As indicated above, the processor 120 or controller 160 is hard-wired or programmed, using software and data structures of the invention, for example, to perform the methodology of the present invention. As a consequence, the system and method of the present invention may be embodied as software which provides such programming or other instructions, such as a set of instructions and/or metadata embodied within a non-transitory computer readable medium, discussed above. In addition, metadata may also be utilized to define the various data structures of a look up table or a database. Such software may be in the form of source or object code, by way of example and without limitation. Source code further may be compiled into some form of instructions or object code (including assembly language instructions or configuration information). The software, source code or metadata of the present invention may be embodied as any type of code, such as C, C++, Matlab, SystemC, LISA, XML, Java, Brew, SQL and its variations (e.g., SQL 99 or proprietary versions of SQL), DB2, Oracle, or any other type of programming language which performs the functionality discussed herein, including various hardware definition or hardware modeling languages (e.g., Verilog, VHDL, RTL) and resulting database files (e.g., GDSII). As a consequence, a "construct", "program construct", "software construct" or "software", as used equivalently herein, means and refers to any programming language, of any kind, with any syntax or signatures, which provides or can be interpreted to provide the associated functionality or methodology specified (when instantiated or loaded into a processor or computer and executed, including the processor 120, 160, for example).

The software, metadata, or other source code of the present invention and any resulting bit file (object code, database, or look up table) may be embodied within any tangible, non-transitory storage medium, such as any of the computer or other machine-readable data storage media, as computer-readable instructions, data structures, program modules or other data, such as discussed above with respect to the memory 125, e.g., a floppy disk, a CDROM, a CD-RW, a DVD, a magnetic hard drive, an optical drive, or any other type of data storage apparatus or medium, as mentioned above.

The network I/O interface circuit(s) 130 are utilized for appropriate connection to a relevant channel, network or bus; for example, the network I/O interface circuit(s) 130 may provide impedance matching, drivers and other functions for a wireline interface, may provide demodulation and analog to digital conversion for a wireless interface, and may provide a physical interface for the processor 120 or controller 160 and/or memory 125 with other devices. In general, the network I/O interface circuit(s) 130 are used to receive and transmit data, depending upon the selected embodiment, such as program instructions, parameters, configuration information, control messages, data and other pertinent information.

The wireless transmitters 135 and/or wireless transceivers 165 also may be implemented as known or may become known in the art, to provide wireless data communication to and/or from any other device, such as wireless or optical communication and using any applicable standard (e.g., any of the IEEE 802.11 standards, Global System for Mobile Communications (GSM), General Packet Radio Service (GPRS), cdmaOne, CDMA2000, Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/TDMA), and Integrated Digital Enhanced Network (iDEN), WCDMA, WiFi, 3G, 4G, and LTE standards, for example and without limitation). In addition, the wireless transmitters 135 and/or wireless transceivers 165 may also be configured and/or adapted to receive and/or transmit signals externally to the systems 200, 400 such as RF or infrared signaling, for example, to receive information in real-time for output on a display, also for example and without limitation.

The network I/O interface circuit(s) 130 may be implemented as known or may become known in the art, to provide data communication between the processor 120 or controller 160 and any type of network or external device, such as wireless, optical, or wireline, and using any applicable standard (e.g., one of the various PCI, USB, RJ 45, Ethernet (Fast Ethernet, Gigabit Ethernet, 300ase-TX, 300ase-FX, etc.), IEEE 802.11, WCDMA, WiFi, GSM, GPRS, EDGE, 3G and the other standards and systems mentioned above, for example and without limitation), and may include impedance matching capability, voltage translation for a low voltage processor to interface with a higher voltage control bus, wireline or wireless transceivers, and various switching mechanisms (e.g., transistors) to turn various lines or connectors on or off in response to signaling from the processor 120 or controller 160. In addition, the network I/O interface circuit(s) 130 may also be configured and/or adapted to receive and/or transmit signals externally to the systems 200, 400 such as through hard-wiring or RF or infrared signaling, for example, to receive information in real-time for output on a display, for example. The network I/O interface circuit(s) 130 may provide connection to any type of bus or network structure or medium, using any selected architecture. By way of example and without limitation, such architectures include Industry Standard Architecture (ISA) bus, Enhanced ISA (EISA) bus, Micro Channel Architecture (MCA) bus, Peripheral Component Interconnect (PCI) bus, SAN bus, or any other communication or signaling medium, such as Ethernet, ISDN, T1, satellite, wireless, and so on.

Numerous advantages of the representative embodiments are readily apparent. The representative apparatus, method and/or system embodiments provide for noninvasive, ambulatory blood pressure and other vital sign monitoring. Representative apparatus and/or system embodiments are comparatively unobtrusive, convenient and easy to use for an individual consumer, while nonetheless being comparatively or sufficiently accurate to obtain meaningful results and actionable information, with a comparatively fast BP acquisition time. Representative apparatus and/or system embodiments also may provide improved compliance by being readily integrable into the user's daily activities. Depending on the selected embodiment, such representative apparatus and/or system embodiments are readily portable and/or wearable to provide ubiquitous monitoring all day and/or night, as may be necessary or desirable.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

With respect to signals, we refer herein to parameters that "represent" a given metric or are "representative" of a given metric, where a metric is a measure of a state of at least part of the regulator or its inputs or outputs. A parameter is considered to represent a metric if it is related to the metric directly enough that regulating the parameter will satisfactorily regulate the metric. A parameter may be considered to be an acceptable representation of a metric if it represents a multiple or fraction of the metric.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

The invention claimed is:

1. A method of determining a blood pressure of a subject human being for ambulatory monitoring, the method comprising:
    using a pressure sensor array having a plurality of pressure sensors spaced-apart in at least two dimensions, applanating an artery;
    receiving a plurality of pressure sensor signals, one or more of the pressure sensor signals having data representing amplitudes of one or more arterial pressure waves;
    determining a frequency content of each of the one or more of the pressure sensor signals having data;
    selecting, based on the determined frequency content, one or more pressure sensor signals that are periodic within a predetermined frequency range to form a first plurality of selected pressure sensor signals;
    selecting one or more periodic pressure sensor signals within a selected deviation of a mean of the first plurality of selected pressure sensor signals to form a second plurality of selected pressure sensor signals;
    using one or more periodic pressure sensor signals from the second plurality of selected pressure sensor signals, determining a systolic blood pressure value and a diastolic blood pressure value.

2. The method of claim 1, further comprising:
    for each periodic pressure sensor signal of the second plurality of selected pressure sensor signals, determining a cross-coherence with each nearest neighbor pressure sensor signal; and
    selecting a periodic pressure sensor signal having a highest mean cross-coherence.

3. The method of claim 2, wherein the step of determining the systolic blood pressure value and the diastolic blood pressure value further comprises:
    determining the systolic blood pressure value as a maximum of the periodic pressure sensor signal having a highest mean cross-coherence; and
    determining the diastolic blood pressure value as a minimum of the periodic pressure sensor signal having a highest mean cross-coherence.

4. The method of claim 1, further comprising:
    performing a first filtering of the plurality of pressure sensor signals to eliminate one or more pressure sensor signals below a predetermined threshold.

5. The method of claim 1, further comprising:
    using one or more periodic pressure sensor signals from the second plurality of selected pressure sensor signals, determining a heart rate.

6. The method of claim 1, wherein the step of determining the systolic blood pressure value and the diastolic blood pressure value further comprises:
    performing a Kalman filtering of the second plurality of selected pressure sensor signals;
    determining the systolic blood pressure value as a maximum of the Kalman filter data; and
    determining the diastolic blood pressure value as a minimum of the Kalman filter data.

* * * * *